US009014810B2

(12) United States Patent
Sauter-Starace et al.

(10) Patent No.: US 9,014,810 B2
(45) Date of Patent: Apr. 21, 2015

(54) IMPLANTABLE DEVICE OF THE NEURAL INTERFACE TYPE AND ASSOCIATED METHOD

(71) Applicant: Commissariat a l'energie atomique et aux energies alternatives, Paris (FR)

(72) Inventors: Fabien Sauter-Starace, Seyssins (FR); Guillaume Charvet, Sassenage (FR); Alim-Louis Benabid, Meylan (FR)

(73) Assignee: Commissariat a l'energie atomique et aux energies alternatives, Paris (FR)

( * ) Notice: Subject to any disclaimer, the term of this patent is extended or adjusted under 35 U.S.C. 154(b) by 0 days.

(21) Appl. No.: 13/754,022

(22) Filed: Jan. 30, 2013

(65) Prior Publication Data

US 2013/0204317 A1    Aug. 8, 2013

Related U.S. Application Data

(60) Provisional application No. 61/597,281, filed on Feb. 10, 2012.

(30) Foreign Application Priority Data

Feb. 2, 2012  (FR) ...................................... 12 50999

(51) Int. Cl.
| | | |
|---|---|---|
| *A61N 1/00* | (2006.01) | |
| *A61N 1/36* | (2006.01) | |
| *A61B 5/00* | (2006.01) | |
| *A61B 5/04* | (2006.01) | |

(52) U.S. Cl.
CPC .......... *A61N 1/36067* (2013.01); *A61B 5/6868* (2013.01); *A61B 5/0031* (2013.01); *A61B 5/04001* (2013.01)

(58) Field of Classification Search
CPC ............ A61B 5/0031; A61B 5/04001; A61B 5/6868; A61N 1/36067
USPC ............................................................ 607/45
See application file for complete search history.

(56) References Cited

U.S. PATENT DOCUMENTS

| | | | | |
|---|---|---|---|---|
| 6,618,623 | B1 * | 9/2003 | Pless et al. ...................... | 607/45 |
| 7,317,947 | B2 * | 1/2008 | Wahlstrand et al. ............ | 607/61 |

(Continued)

FOREIGN PATENT DOCUMENTS

| | | |
|---|---|---|
| WO | WO 2011/067297 A1 | 6/2011 |
| WO | WO 2011/123150 A2 | 10/2011 |

OTHER PUBLICATIONS

French Preliminary Search Report issued Sep. 12, 2012 in Patent Application No. 1250999 with English Translation of Category of Cited Documents.

(Continued)

*Primary Examiner* — George Manuel
(74) *Attorney, Agent, or Firm* — Oblon, McClelland, Maier & Neustadt, L.L.P.

(57) ABSTRACT

The main object of the invention is an implantable device of the neural interface type for processing signals, including:
 a case intended to be held at least partially in a cavity formed on the cranium of a human or animal,
 an electronic circuit positioned in the case (B), and
 a system of electrodes coupled electrically to the electronic circuit,
wherein the device includes a signal transmission sleeve, extending from the periphery of the case.

24 Claims, 5 Drawing Sheets

(56) References Cited

U.S. PATENT DOCUMENTS

Figure 1:
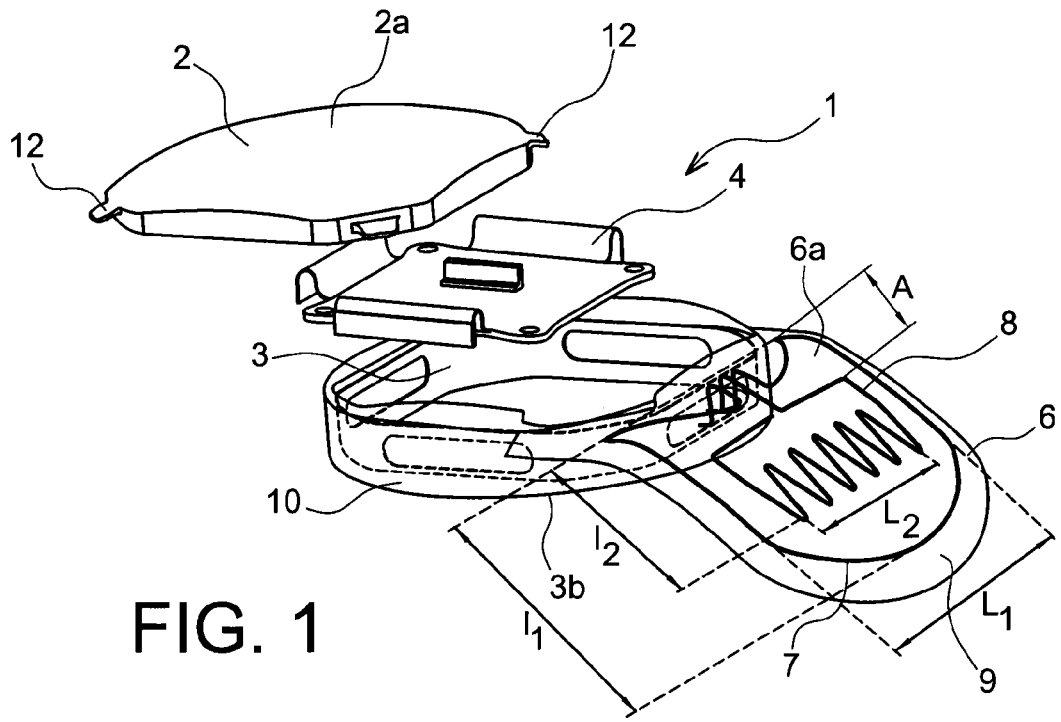

| | | | |
|---|---|---|---|
| 7,346,391 B1 * | 3/2008 | Osorio et al. | 607/2 |
| 7,930,035 B2 | 4/2011 | DiLorenzo | |
| 2007/0161919 A1 | 7/2007 | DiLorenzo | |
| 2007/0162086 A1 | 7/2007 | DiLorenzo | |
| 2007/0208212 A1 | 9/2007 | DiLorenzo | |
| 2008/0119900 A1 | 5/2008 | DiLorenzo | |
| 2008/0234598 A1 | 9/2008 | Snyder et al. | |
| 2009/0099627 A1 | 4/2009 | Molnar et al. | |
| 2010/0023089 A1 | 1/2010 | DiLorenzo | |
| 2011/0319785 A1 | 12/2011 | Snyder et al. | |
| 2012/0108998 A1 | 5/2012 | Molnar et al. | |
| 2012/0203131 A1 | 8/2012 | DiLorenzo | |

OTHER PUBLICATIONS

Sun-Il Chang et al., "BioBolt: A Minimally-Invasive Neural Interface for Wireless Epidural Recording by Intra-Skin Communication", Symposium on VLSI Circuits Digest of Technical Papers, 2011, pp. 146-147.

* cited by examiner

IMPLANTABLE DEVICE OF THE NEURAL INTERFACE TYPE AND ASSOCIATED METHOD

TECHNICAL FIELD

The present invention relates to the field of implantable devices in contact with the human or animal brain for processing neural signals. It relates in particular to brain implants known by the name of "neural interfaces", allowing communication between the brain and an electronic device, notably communication of neural signals recorded by electrodes positioned in the brain.

The invention thus relates to an implantable device of the neural interface type, together with an associated manufacturing method.

State of the Prior Art

Many systems which can be implanted in the human or animal brain for reading, recording and/or controlling neural signals have been designed over the past years, notably in order to diagnose, prevent, assist, improve or repair human or animal cognition functions or defective actions.

Such systems have, for example, found applications in the treatment of epileptic fits, in the attenuation of symptoms of Parkinson's disease, in measures to treat depression, and in the treatment of other medical problems.

These systems can notably allow the control of effectors for applications known as "Brain-Computer Interface" (BCI) applications. Applications of the BCI type can generally allow control of actuators by means of neural signals collected by electrodes implanted in or on the brain. Another expression used is control by thought.

The various brain implants known from the prior art for processing neural signals can be classified according to the area of implantation.

Electrocorticography (EcoG) technology characterises devices allowing graphical recording of brain activity due to electrodes, distributed in a matrix, placed in direct contact with the cortex under the dura mater. The cortical signals measured are processed by electronic means. This technique is invasive, since it requires that a craniotomy is carried out on the individual to be examined, i.e. a surgical incision in the cranium.

Electroencephalography (EEG) constitutes another method of brain exploration which measures the electrical activity of the brain by electrodes positioned on the scalp. This technique is non-invasive.

Finally, two other technologies for measuring neural signals, and in particular neural potential, are also known, under the names "Single Unit Action Potential" (SUAP) and "Local Field Potential" (LFP). They are based on the principle of penetration of point electrodes in the brain, in particular in the cortex in order to make the measurement.

Electronic means enabling the neural signals captured by the electrodes to be received can also be located outside the brain and connected to the electrodes by wired connections. However, to optimise the signal-to-noise ratio, it has proved of interest to seek to position them as close as possible to the signal recording area, and thus also to implant them within the brain.

The article entitled "BioBolt: A Minimally-Invasive Neural Interface for Wireless Epidural Recording by Intra-Skin Communication", Sun-Il Chang et al, 2011 Symposium on VLSI Circuits Digest of Technical Papers, pages 146-147, and international application WO 2011/123150 describe a neural interface which includes an enlarged head positioned at the top of a threaded body. The head is intended to come into contact with the cranium, whereas the threaded body is designed to be inserted into a bore of the same diameter formed in the bone of the cranium. An electrode is positioned at the base of the threaded body, and is coupled electrically to an electrical circuit located in the widened head. The electrical circuit can allow the electrical signals collected by the electrode to be preamplified and/or digitised, and then transmitted to remote electronic or computational means, by a wired or radio link, for processing.

The brain implant devices described above, which involve invasive implantation techniques, are devices positioned in direct contact with the skin; the latter usually covers the upper parts of the devices. This direct contact with the skin can lead to risks of non-negligible lesions and/or infection of the skin, particularly at the junction between the cranium and the upper portion of the device when the latter is held in a cavity of the cranium formed by craniotomy. In addition, integration of these implantable devices in the brain of an individual may lead to substantial discomfort for the individual in the implantation area, relating to how comfortable it is for the user. It can also be unsightly and give the cranium a non-uniform external appearance.

DESCRIPTION OF THE INVENTION

There is a requirement to design an implantable device of the neural interface type for processing neural signals enabling the medical risks relating to its use to be minimised, notably the risks of lesions and/or infection of the body of an individual, and notably of the skin covering the cranium of the individual. There is also a requirement to allow uniform integration of such a device in the brain in order to obtain aesthetic and physical comfort for the individual.

The invention seeks to address all or a proportion of these requirements.

One object of the invention is therefore, according to one of its aspects, an implantable device of the neural interface type for processing signals, notably neural signals, including:
  a case intended to be held at least partially in a cavity formed on the cranium of a human or animal,
  an electronic circuit for processing signals positioned in the case, and
  a system of electrodes coupled electrically to the electronic circuit, characterised in that the case includes an upper face, intended to come into contact with the skin, the surface of which is appreciably convex.

"Appreciably convex" is taken to mean that the surface of the upper face is convex, or at the very least appears convex to the naked eye.

The convexity of the surface of the upper face of the case can be determined so as to reproduce at least partially the curvature of the cranium in the area of the said cavity, and to provide an appreciable surface continuity between the upper face of the case and the adjacent surface areas of the cranium. The curvature of the upper face of the case can, for example, be equivalent to the actual curvature of the cranium of the human or animal; such curvature varies according to the cranium and the area of implantation. The radius of curvature can thus vary between 50 and 200 mm.

By virtue of the invention the device can be incorporated uniformly in the individual's cranium, and have zero or near-zero protrusions on its upper face in contact with skin, such that it does not lead to risks of lesions and/or infection of the skin. The device can also be incorporated in the cranium such that it is flush with it, greatly reducing the habitual unevenness in the smooth surface found at the junction between the cranium and the upper face of the device, such that the device is as discreet as possible and tends to be visually undetectable.

The device according to the invention can also include one or more of the following characteristics, taken in isolation or in all possible technical combinations.

The case can be formed by assembling an upper portion and a lower portion, notably by welding.

The upper portion can include a lip extending from the upper face of the case, and defining the lateral surface of the upper portion, where the lip is intended to be inserted in the lower portion of the case, abutting against the lateral face of the lower portion.

The lip can extend along the entire perimeter of the upper portion.

The upper portion of the case can include retaining brackets, which notably project over the lip, intended to be supported on the cranium of the human or animal.

The upper portion can have a roughly circular or polygonal shape, and notably a square shape.

Planes can be formed at angles, notably each angle, of the upper portion, and the retaining brackets can notably project from these planes.

The lower portion can have a lower face and a lateral face, which together define a bowl-shaped recess to hold the electronic circuit.

The lateral face of the lower portion can be perforated, and notably have apertures to allow the passage of electrical contacts to couple the electronic circuit electrically with the system of electrodes.

The lower portion can have a roughly circular or polygonal shape, and notably a square shape.

The case, notably the upper portion and/or the lower portion, can be overmoulded by an overmoulding material, notably a biocompatible silicon resin.

The largest transverse dimension of the case can be between 1 and 5 cm.

The thickness of the case can be between 0.3 and 1 cm, and notably between 0.5 and 1 cm.

The case can be manufactured from a rigid, biocompatible material, for example it can be manufactured from titanium or ceramic.

The case can be hermetic, notably in order to prevent any intrusion of liquid inside the case.

The system of electrodes can be attached under the case, on the lower face of the lower portion of the case.

The system of electrodes can be incorporated in the case's external perimeter, notably in the external perimeter of the lower portion of the case.

The system of electrodes can include electrodes positioned according to a predetermined matrix, notably a network, whether or not regular.

The system of electrodes can include electrodes for recording signals, notably neural signals, and/or stimulation electrodes. The stimulation electrodes can, for example, allow electrical signals to be emitted in the brain, for example to treat various illnesses such as Parkinson's disease, depression, migraine and/or obesity.

The electronic circuit can be an electronic circuit for processing neural signals measured by recording electrodes and/or an electronic circuit for producing electrical stimulation signals by stimulation electrodes.

The device can also include a signal transmission sleeve extending from the periphery of the case, notably from the periphery of the lower portion of the case.

"Transmission of signals" is taken to mean the transmission of measured neural signals and/or electrical stimulation signals, and/or the transmission of signals towards the electronic circuit, for example remote power feeding signals and/or control signals controlling these means.

The sleeve can thus include at least one transmission antenna, for the exchange of emission and/or reception data, and/or at least one remote power feeding antenna. In particular, the sleeve can include a transmission antenna and a remote power feeding antenna, where both antennae are coplanar and are positioned such that one is incorporated in the other.

The sleeve can be made from a flexible biocompatible material, notably from a silicon-type elastomer.

The sleeve can be sufficiently thin to be slid between the cranium and the skin of the scalp.

The sleeve's thickness can notably be less the further it is from the case. In other words, the thickness of the sleeve can be reduced in proportion to the distance from the periphery of the case. The thickness of the sleeve can, for example, be between 1 and 3 mm, for example less than 1.5 mm, still better 1 mm, and even better still 0.7 mm. The thickness of the sleeve can be constant over a predetermined distance from the case, and then gradually reduce until the end of the sleeve.

The sleeve can have a Shore A hardness less or equal to 50.

The sleeve can have an appreciably convex (or curved) upper surface, such that it at least partially reproduces the curvature of the cranium and/or that of the scalp in the area where it is implanted, and such that it provides an appreciable surface continuity between the upper face of the case and the upper face of the sleeve.

In particular, the upper surface of the sleeve can be connected to the upper face of the case in continuous fashion, such that it has a roundness closely following the shape of the scalp and/or that of the cranium at the interface between the case and the sleeve.

The upper surface of the sleeve and the upper face of the case can be tangential relative to one another at their interface.

Another object of the invention, according to another of its aspects, is a method for implanting a device as previously defined in a cavity formed on the cranium of a human or animal, in which the device is placed in the cavity such that the upper face of the case and the surface portions of the cranium adjacent to the case appreciably form a continuous surface.

A "continuous surface" is taken to mean that the junction between the upper face of the device, notably that of the case, and the adjacent surface portions of the cranium has appreciably no additional thickness. In particular, the junction between the upper face of the device and the cranium may have a smooth appearance. Generally, at the said junction, the plane tangential to the upper face of the device is thus parallel, or appreciably merged, with the plane tangential to the cranium in which the upper face is inserted.

Another object of the invention, according to one of its aspects, is a method for manufacturing a device, and notably a case, as previously defined, in which the convexity of the upper face of the device's case is determined from measurements of convexity previously made on the cranium of a human or animal.

Another object of the invention, according to one of its aspects, is a method for manufacturing an implantable device of the neural interface type for the processing of signals, including:

a case intended to be held at least partially in a cavity formed on the cranium of a human or animal, an electronic circuit for processing signals positioned in the case, and a system of electrodes coupled electrically to the electronic circuit, the case including an upper face, intended to come into contact with the skin, the surface of which is appreciably convex, in which the convexity of the upper face of the device's case is determined from measurements of convexity previously made on the cranium of a human or animal.

The measurements of convexity can be made at the location where the device is implanted, notably in the area of the cranium where the cavity for implantation will be formed, for example by craniotomy.

Another object of the invention is, according to another of its aspects, an implantable device of the neural interface type for processing signals, notably neural signals, including:
- a case intended to be held at least partially in a cavity formed on the cranium of a human or animal,
- an electronic circuit for processing signals positioned in the case, and
- a system of electrodes coupled electrically to the electronic circuit, characterised in that it includes a sleeve for transmitting signals extending from the periphery of the case.

The electrodes can be, for example, electrodes recording neural or stimulation signals.

Another object of the invention, according to another of its aspects, is a transmission sleeve for an implantable device of the neural interface type, including at least one transmission antenna and/or at least one remote power feeding antenna.

Another object of the invention, according to another of its aspects, is an implantable device of the neural interface type for processing signals, notably neural signals, including:
- a case intended to be held at least partially in a cavity formed on the cranium of a human or animal,
- an electronic circuit for processing signals positioned in the case, and
- a system of electrodes coupled electrically to the electronic circuit, characterised in that the system of electrodes is contained in the external perimeter of the case, the case including in particular an upper face, intended to come into contact with the skin, the surface of which is appreciably convex.

The device, and notably the sleeve of the device, can include one or more of the abovementioned characteristics.

BRIEF DESCRIPTION OF THE ILLUSTRATIONS

Figure 2:
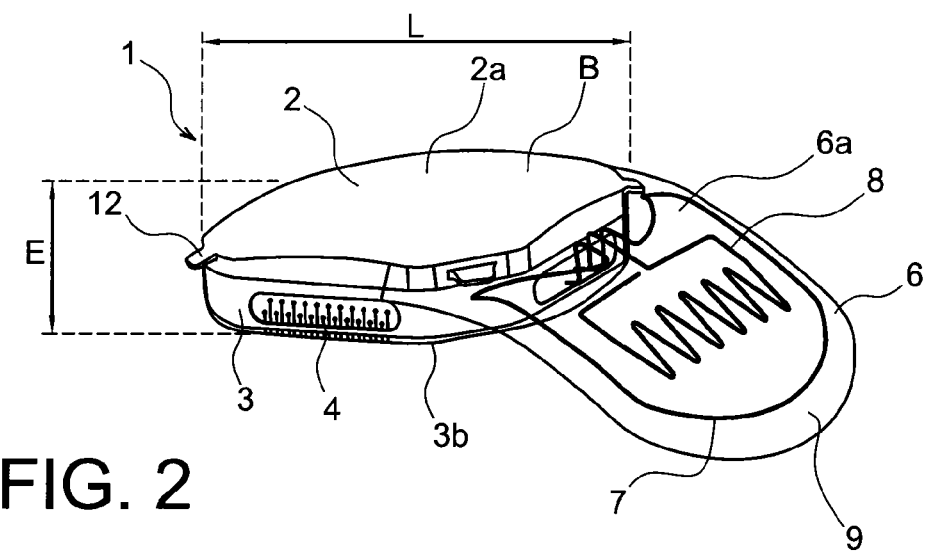
Figure 3:
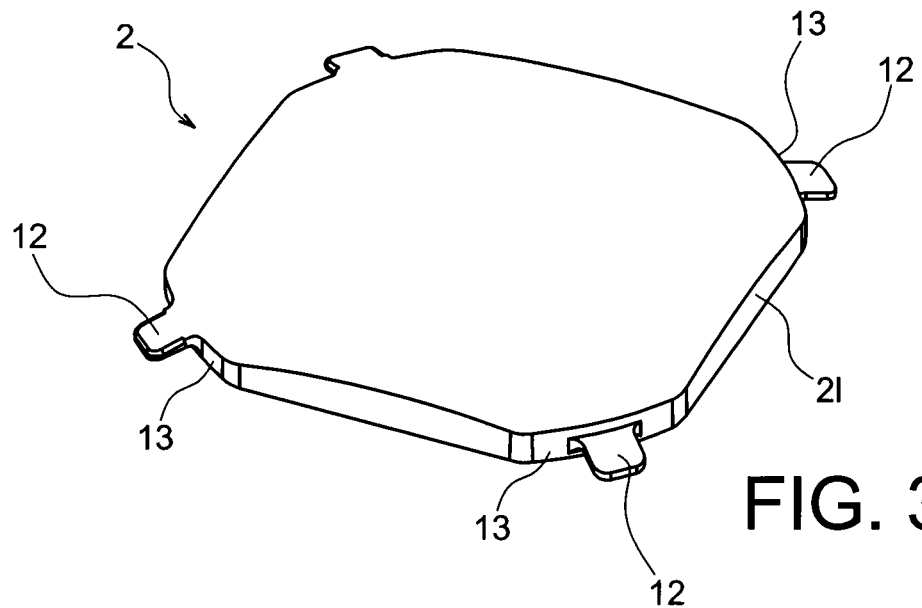
Figure 4:
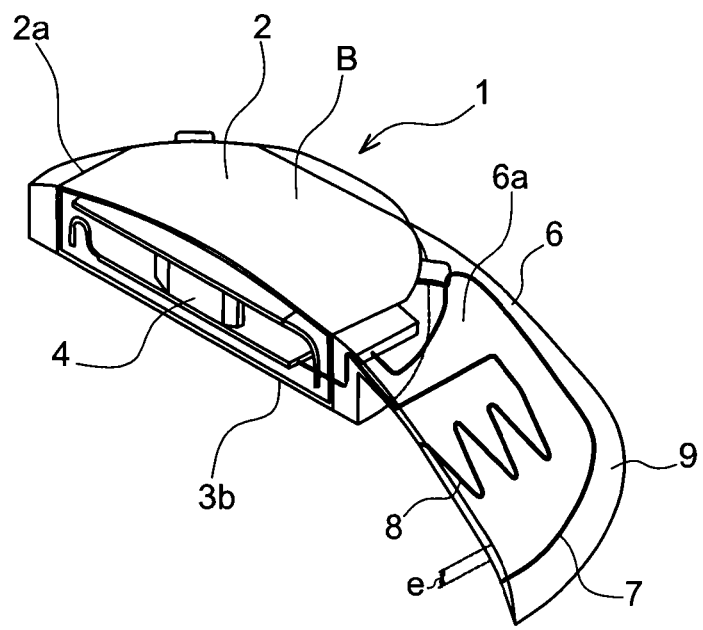
Figure 5:
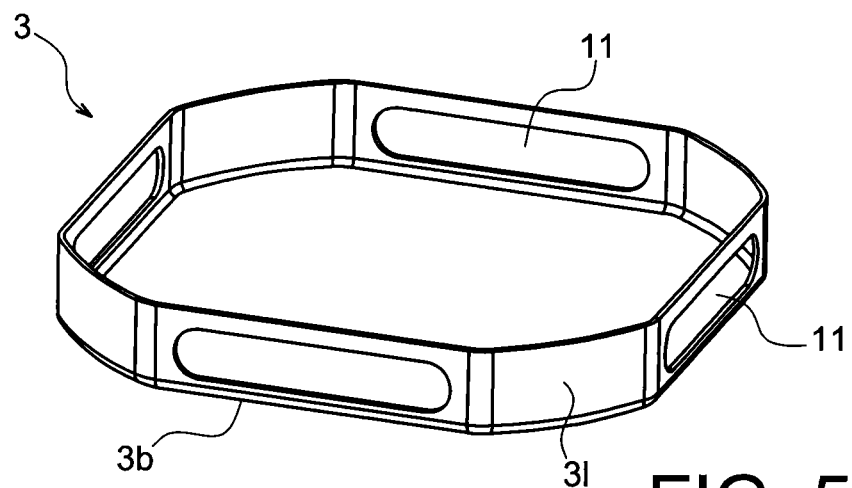
Figure 6:
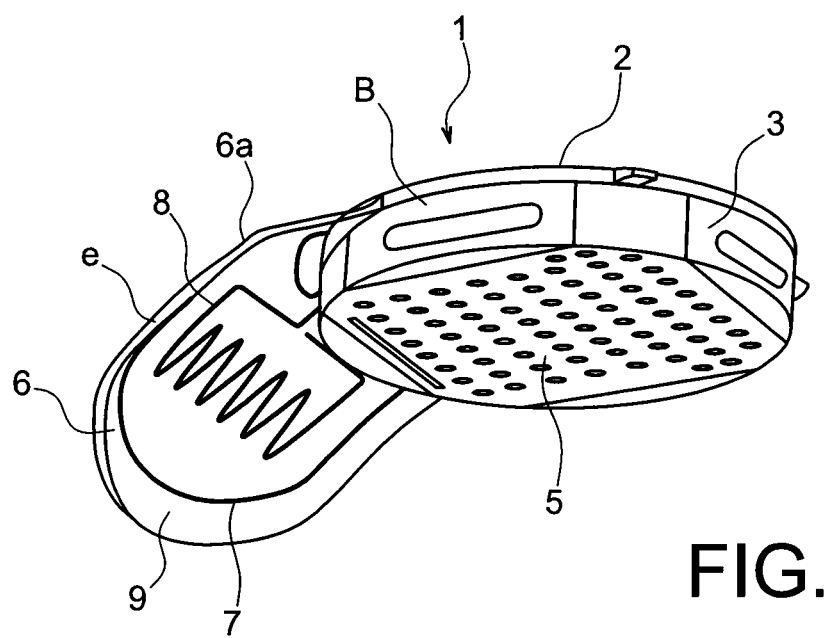
Figure 7:
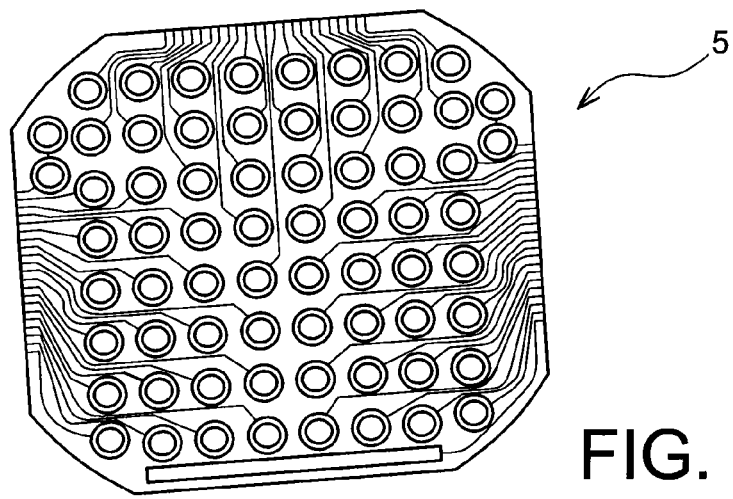
Figure 8A:
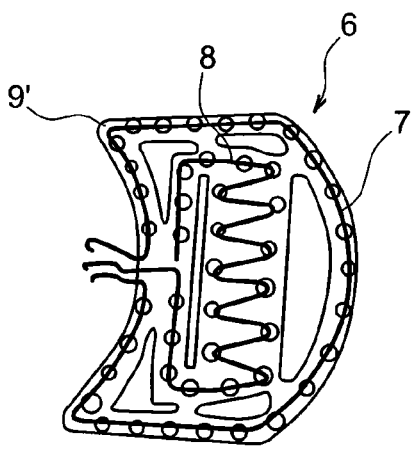
Figure 8B:
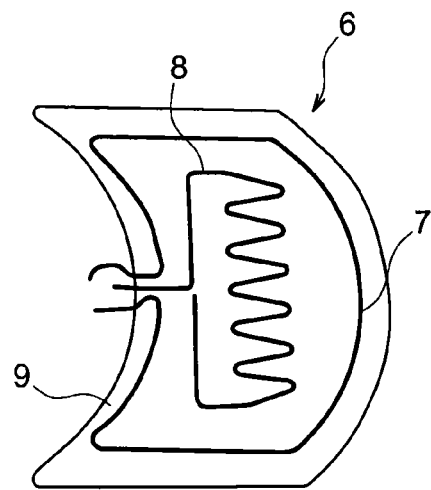
Figure 9:
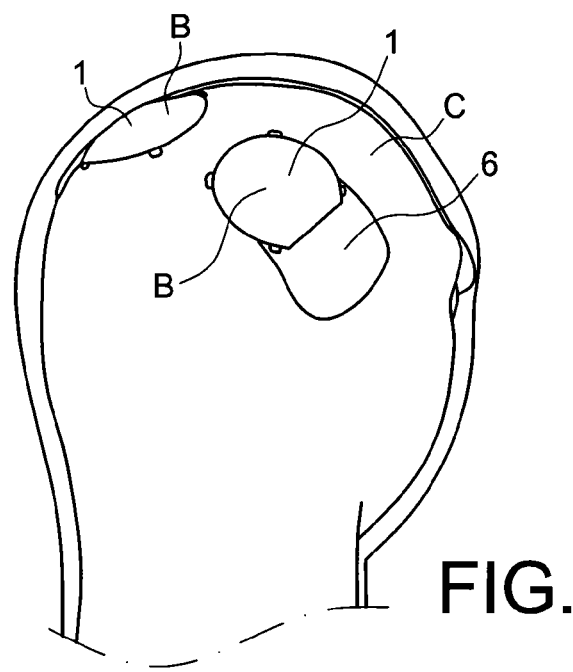
Figure 10:
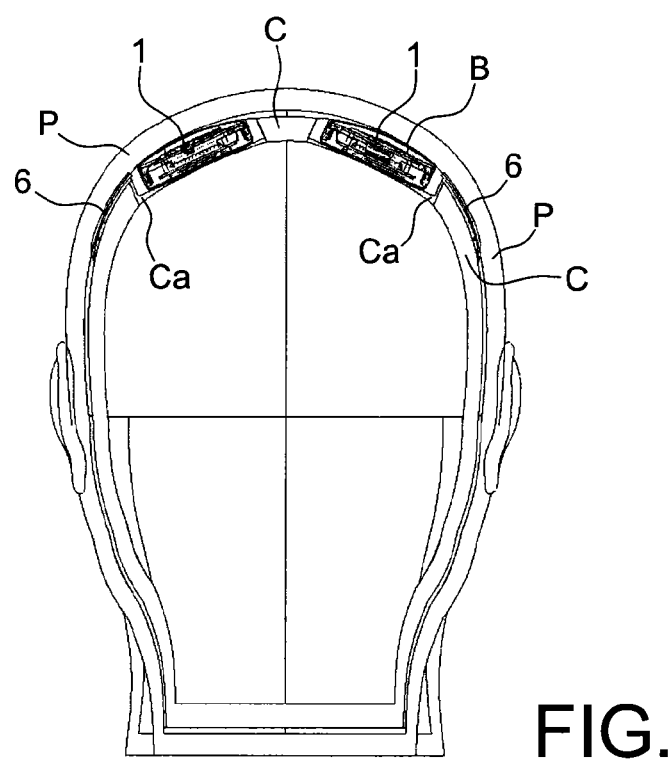

The invention will be able to be better understood on reading the detailed description, below, of a non-restrictive example implementation of it, and also on examining the appended illustration, in which:

FIG. 1 is an exploded perspective representation of an example of an implantable device according to the invention, FIG. 2 represents a perspective view of the device of FIG. 1 in an assembled configuration, FIG. 3 represents a perspective view of the upper portion of the case of the device of FIGS. 1 and 2, FIG. 4 is a perspective section view of the device of FIGS. 1 and 2, FIG. 5 represents a perspective view of the lower portion of the case of the device of FIGS. 1 and 2, FIG. 6 represents a perspective view, as seen from underneath, of the device of FIGS. 1 and 2, FIG. 7 represents, seen from the front, the system of electrodes of the device of FIGS. 1 and 2, FIGS. 8a and 8b illustrate two steps of the manufacture of the sleeve of the device of FIG. 1, and FIGS. 9 and 10 illustrate, respectively, a perspective view and a section view of the implantation of two devices according to the invention on the cranium of a human.

In all these figures, identical references can designate identical or comparable elements.

DETAILED ACCOUNT OF A PARTICULAR EMBODIMENT

In FIGS. 1 and 2 an example of an implantable device 1 in accordance with the invention has been represented.

Device 1 includes a case B within which an electronic circuit 4 are held. Case B is formed by assembling an upper portion 2 and of a lower portion 3, which can be seen respectively in isolation in FIGS. 3 and 5.

In addition, device 1 includes a system of electrodes 5, as can be seen in FIG. 6, and in isolation in FIG. 7.

Device 1 also includes a transmission sleeve 6, which will be described in detail below.

Implantable device 1, and notably case B of device 1, is intended to be implanted in contact with the brain of an individual, notably in order to record and process the brain's neural signals. FIGS. 9 and 10 illustrate schematically the implantation of two devices 1 in accordance with the invention, respectively in two cavities Ca formed on cranium C of a human, for example following a craniotomy operation. Case B of a device 1 is held in a cavity Ca, while sleeve 6 of this device 1 is inserted between cranium C and skin P of the scalp.

In accordance with the invention, case B includes an upper face 2a, intended to come into contact with skin P, the surface of which is appreciably convex. The convexity of the surface of upper face 2a can enable upper portion 2 of case B, which is intended to come into contact with skin P, to be given a rounded shape in order to reproduce, at least partially, or totally, the curvature of cranium C in the area of cavity Ca which is formed in it and, furthermore, to provide an appreciably continuous surface between upper face 2a of case B and the surface portions of cranium C which are adjacent to device 1. The convexity of upper face 2a can therefore allow the interface between device 1 and the surface portions of cranium C which are adjacent to it to be smoothed.

Upper face 2a of case B can advantageously allow the shape of cranium C to be followed closely at the position of cavity Ca which is formed in it, in order to reduce, or to make non-existent, the protrusions on the surface of upper face 2a of case B, and in particular at the junction between upper face 2a of case B and the surface portions of cranium C which are adjacent to device 1. In this manner, the risk of lesions and/or infection of the skin, in particular at this junction, is greatly reduced. Device 1 can therefore be implanted in contact with the brain for a long period, whilst limiting the risks for the individual. The convexity of upper face 2a of case B can indeed enable device 1, and notably upper face 2a of upper portion 2 of case B, to be flush with the bone of cranium C at the periphery of cavity Ca.

Upper face 2a of case B can have a convex or multiconvex surface, and in particular a biconvex surface; it may have, for example, convexity in two orthogonal directions. The convexity of the surface of upper face 2a of case B can, for example, be determined in relation to the curvature of cranium C, notably in the area of cavity Ca before it is formed, for example by craniotomy. Upper face 2a of case B can in particular have appreciably the same curvature as that of cranium C in the region where cavity Ca is formed.

Upper portion 2 of case B includes a convex upper face 2a, as described above, and also, as can be seen in FIG. 3, a lip 21 extending from upper face 2a defining the lateral surface of upper portion 2. Lip 21 extends in particular around the entire perimeter of upper portion 2 in this example but, as a variant, lip 21 may extend only partly around the perimeter of upper portion 2 of case B. Lip 21 is intended to be inserted in lower portion 3 of case B, and abut, in particular on the inner side, against lateral face 31 of lower portion 3.

Upper portion 2 of case B also includes retaining brackets 12, as can be seen in FIG. 3, which protrude over lip 21. Retaining brackets 12 are, for example, positioned at corners of upper portion 2. Retaining brackets 12 are notably intended to be supported on cranium C of the individual, in the areas of the portions of cranium located on the periphery of cavity Ca. In this way, retaining brackets 12 can allow device 1 to be held on cranium C, preventing the latter from sinking into cranium C in the area of cavity Ca. Retaining brackets 12 can be held on cranium C by any attachment means, and notably by intracranial screws. The thickness of retaining brackets 12 can be sufficiently low that no local additional thickness is caused at the interface between device 1 and the portions of cranium C adjacent to device 1 which may cause risks of lesions and/or infections of skin P.

Lower portion 3 has a lower face 3b and a lateral face 31, which together define a bowl-shaped recess to hold the electronic circuit 4. Upper face 2a of upper portion 2 is intended to be applied against skin P of the scalp, while lower face 3b of lower portion 3 is directed towards the cortex of the individual's brain. Lower portion 3 can hold system of electrodes 5, as can be seen in FIG. 6. Lateral face 31 of lower portion 3 is perforated. It includes in particular apertures 11, which are for example of oblong shape, of which there are for example four such, as in this example. Apertures 11 can allow the passage of electrical contacts to couple the electronic circuit 4 electrically with system of electrodes 5.

Upper portion 2 forms a cover intended to close the recess formed in lower portion 3 of device 1 by lateral face 31 and lower face 3b of lower portion 3. Upper portion 2 can in particular be welded on to lower portion 3 of case B.

Upper portion 2 and/or lower portion 3 can be roughly circular in shape, and in particular square in shape. In this case retaining brackets 12 of upper portion 2 can be located at all four corners of upper portion 2. Planes 13 can be formed at each angle of upper portion 2, notably at each angle of lip 31, and retaining brackets 12 can project from these planes 13.

Lateral face 31 of lower portion 3 can also be roughly circular in shape, and in particular square in shape. In this case, apertures 11 can be formed on each of the four sides defined by lateral face 31.

Case B, notably upper portion 2 and/or lower portion 3, can be overmoulded by an overmoulding material 10, notably a biocompatible silicon resin. In FIG. 1, lower portion 3 is overmoulded by such an overmoulding material 10. Overmoulding material 10 can enable the external perimeter of case B, and notably of upper portion 2 and/or of lower portion 3, to be modified, for example by giving it an appreciably cylindrical shape.

The largest transverse dimension of cavity Ca formed in cranium C of the individual can be between 1 and 5 cm. Case B of implantable device 1 can consequently have a largest transverse dimension L of between 1 and 5 cm; it can, for example, be approximately 47 mm, as in this example. In addition, thickness E of case B can, for example, be between 0.3 and 1 cm, notably between 0.5 and 1 cm; it can, for example, be equal to approximately 0.7 cm.

Case B is preferably manufactured from a rigid, biocompatible material; it can, for example, be manufactured from titanium or ceramic. In addition, case B is preferably hermetic, notably in order to prevent any intrusion of liquid, or gas, inside case B.

The electronic circuit 4 can thus be held hermetically inside case B. The electronic circuit 4 can be insulated electrically from case B.

The electronic circuit 4 are coupled electrically to system of electrodes 5.

The electronic circuit 4 can, for example, include a preamplifier, an analog-digital converter and/or means for the transmission of measured data concerned with the neural signals.

The electronic circuit 4 can include a power system and/or a circuit able to generate a power signal from a signal detected by a remote feeding power antenna.

FIG. 6 represents the positioning of system of electrodes 5 under implantable device 1, in lower face 3b of lower portion 3 of case B.

FIG. 7 represents, seen from the front, system of electrodes 5.

System of electrodes 5 is thus preferably positioned outside case B. In particular, lower face 3b of case B and system of electrodes 5 can be partially, or better still totally, positioned vertically above one another.

System of electrodes 5 preferably includes electrodes of the EcoG type using the previously described electrocorticography technology.

The electrodes of system of electrodes 5 can be arranged in a predetermined matrix, as can be seen in FIG. 7, for example as a network of lines and columns, whether or not regular. In particular, as represented in FIG. 7, network of electrodes 5 can be arranged in a matrix comprising 64 electrodes.

System of electrodes 5 is advantageously securely attached to case B; it is in particular attached to lower face 31 of case B. In this manner, the invention can allow the positioning of the electrodes on the brain to be controlled, unlike the electrodes of the prior art, which are, for example, produced on a flexible substrate and are positioned at some distance from the case. The invention can also allow use of a wired connection between the matrix of electrodes and the case to be avoided.

System of electrodes 5 can be incorporated in the external perimeter of case B, notably in the external perimeter of lower portion 3 of case B. The electrode recording area and the accessible area of the brain where neural signals are recorded, formed by cavity Ca during a craniotomy, for example, may thus coincide.

According to a variant embodiment, system of electrodes 5 may include intracortical electrodes, i.e. electrodes able to penetrate the cortex, notably electrodes based on the previously described LFP technology. Use of intracortical electrodes, although based on a more invasive technology than electrocorticography technology, may enable better spatial resolution to be obtained.

As another variant, system of electrodes 5 may include a network formed of EcoG electrodes and intracortical electrodes.

The positioning of system of electrodes 5 may, for example, be defined using prior examinations undertaken on the individual.

The electrical coupling between system of electrodes 5 and the electronic circuit 4 held inside case B may be accomplished in hermetic passages positioned at previously described apertures 11 of lower portion 3. Each hermetic passage may include a metal body, notably a titanium body, for example a blade, having one or more apertures. Each aperture may include a metal spindle, notably made of platinum or platiniridium, which can be sheathed with glass or a ceramic, for example ruby, to provide the electrical insulation between the metal spindle and the metal body. In the represented example embodiment each hermetic passage includes 23 apertures, and therefore 23 spindles. In the interfaces between the metal body and the sheathing, for example between the titanium and the ruby, and between the spindle and the sheathing, for example between the platinum and the ruby, gold may be deposited in order to ensure hermeticity. The passages can also the embedded in an overmoulding material, for example an insulating epoxy or acrylic resin.

According to another aspect of the invention, implantable device 1 includes a signal transmission sleeve 6. The function of this sleeve 6 is to transmit signals from and/or towards electric means 4 by a wireless connection.

Sleeve 6 may extend from the periphery of device 1, and notably from the periphery of lower portion 3 of case B, as represented in FIG. 1.

Unlike case B, sleeve 6 may be made from a flexible, biocompatible material. Sleeve 6 may, for example, be made from a silicon resin, for example the silicon resin sold by the company NUSIL with the reference MED6210 or MED6215.

Sleeve 6 is intended to be inserted between cranium C and skin P of the scalp, as an extension of upper surface 2*a* of case B, as can be seen in FIGS. 9 and 10.

Sleeve 6 can have a sufficiently low thickness e to be slid between cranium C and skin P of the scalp. Thickness e of sleeve 6 can notably be less the further it is from case B. In other words, thickness e of sleeve 6 can be reduced in proportion to the distance from the periphery of case B.

Thickness e of sleeve 6 can, for example, be between 1 and 3 mm, for example less than 1.5 mm, still better 1 mm, and even better still 0.7 mm. Thickness e of sleeve 6 can be constant over a predetermined distance from case B, and then gradually reduce until the end of sleeve 6. In the example in question, sleeve 6 has, for example, a thickness e of approximately 1.5 mm over a maximum distance A of 3 cm relative to case B; thickness e then gradually reduces until it reaches 0.2 mm at the end of sleeve 6.

Sleeve 6 may have a Shore A hardness equal to approximately 50. Sleeve 6 can thus have a flexibility allowing satisfactory adaptation when implanted between cranium C and the scalp.

Sleeve 6 can have an appreciably convex (or curved) upper surface 6*a*, such that it at least partially reproduces the curvature of the cranium and that of the scalp in the area where it is implanted, and such that it provides an appreciable surface continuity between upper face 2*a* of case B and upper face 6*a* of sleeve 6. In particular, upper surface 6*a* of sleeve 6 can be connected to upper face 2*a* of case B in continuous fashion, such that it has a roundness closely following the shape of the scalp and that of the cranium at the interface between case B and sleeve 6. Upper surface 6*a* of sleeve 6 and upper face 2*a* of case B can be tangential relative to one another at their interface. The invention can thus enable the risks of lesions and/or infection, notably of the skin, to be minimised, at the interface between sleeve 6 and case B.

Sleeve 6 can include at least one transmission antenna, for the exchange of emission and/or reception data, and/or at least one remote power feeding antenna. In particular, sleeve 6 can include at least one radio connection transmission antenna, to communicate with the exterior. When sleeve 6 includes two antennae, notably one transmission antenna and one remote power feeding antenna, both antennae are preferably coplanar and positioned such that one is contained within the other. Having coplanar antennae contained one within the other can enable the total thickness of sleeve 6 to be limited significantly.

The antenna or antennae can be connected to the electronic circuit 4 through an aperture 11 of lower portion 3 as previously described, or through a passage sealed by a biocompatible insulating resin.

In the described example embodiment, sleeve 6 advantageously includes a remote power feeding antenna 7 and an antenna 8 for transmitting the neural signals processed by the electronic circuit 4, where both antennae are coplanar and remote power feeding antenna 7 surrounds transmission antenna 8, and where the latter is contained within remote power feeding antenna 7.

More specifically, sleeve 6 includes a High-Frequency (HF) remote power feeding antenna 7 of 13.56 MHz and an Ultra High Frequency (UHF) transmission antenna 8 of 402 to 405 MHz.

By virtue of the invention, moving the antenna or antennae contained in sleeve 6 further away from case B holding the electronic circuit 4 can enable the shielding effects of the material constituting case B, i.e. the effect of attenuation of the electric field due to the presence of moving electrical charge carriers within the material of case B, to be limited. Indeed, since sleeve 6 is made from a non-metallic material, for example a silicon overmoulding in which the antenna or antennae are embedded, and since case B is made from a metallic material, notably titanium, moving sleeve 6 further away from case B enables a possible shielding effect to be limited. In addition, placing the antenna or antennae under the scalp can enable data to be transmitted from the exterior and/or towards the exterior, whilst minimising attenuation.

As can be seen in FIG. 1, maximum distance $I_1$ between case B and the end of remote power feeding antenna 7 may be approximately 3 cm. Similarly, maximum distance $I_2$ between case B and the end of transmission antenna 8 may be approximately 1.5 cm.

Maximum width (or separation) $L_1$ of remote power feeding antenna 7 may be approximately 4 cm. Similarly, maximum width $L_2$ of transmission antenna 8 may be approximately 3 cm.

Each antenna may include a metal wire, notably a platinum wire, of diameter, for example, equal to 500 µm. Each antenna can delimit a given area. For example, remote power feeding antenna 7 can cover an area of approximately 10 cm$^2$.

FIGS. 8*a* and 8*b* illustrate respectively the two steps of manufacture of sleeve 6 of device 1 according to the invention.

During the step illustrated in FIG. 8*a*, each antenna 7 and 8 is covered with a first overmoulding 9', for example using a silicon resin, so as to rigidify the antenna. Overmoulding 9' can consist of a sheath of approximate diameter 1.5 mm around the wire constituting the antenna.

During the step illustrated in FIG. 8*b*, each antenna is covered with a second overmoulding 9, for example with the same material as with the first overmoulding 9', in order to obtain sleeve 6. Second overmoulding 9 can be made over the whole of antennae 7 and 8 and the space separating antennae 7 and 8.

The invention is, naturally, not limited to the example embodiment which has just been described.

In particular, system of electrodes 5 can include stimulation electrodes, where the electrical stimulation signals are then generated by the electronic circuit 4 located in case B. These means can then include stimulation signal generators.

The expression "including a" must be understood as being synonymous with "including at least one", unless the contrary is specified.

The invention claimed is:

1. An implantable device of a neural interface type for processing signals, including:
    a case intended to be held at least partially in a cavity formed on a cranium of a human or animal,
    an electronic circuit positioned in the case for processing the signals,
    a system of electrodes coupled electrically to the electronic circuit, and
    a signal transmission sleeve attached to the case and configured to extend outward from a periphery of the case along a direction that follows a curvature of the cranium and/or that of a scalp in an area where it is implanted.

2. The device according to claim 1, wherein the case includes an upper face, intended to come into contact with skin, a surface of which is appreciably convex.

3. The device according to claim 1, wherein the signal transmission sleeve includes at least one transmission antenna and/or one remote power feeding antenna.

4. The device according to claim 1, wherein the system of electrodes is contained in an external perimeter of the case.

5. The device according to claim 1, wherein the signal transmission sleeve includes a transmission antenna and a remote power feeding antenna, where both antennae are coplanar and positioned such that one is contained within the other.

6. The device according to claim 1, wherein a thickness of the signal transmission sleeve is less the further it is from the case.

7. The device according to claim 1, wherein the signal transmission sleeve includes an upper face and the case includes an upper face, the upper face of the signal transmission sleeve and the upper face of the case being tangential relative to one another at their interface.

8. The device according to claim 1, wherein the signal transmission sleeve has an appreciably convex upper surface, such that it at least partially reproduces the curvature of the cranium and/or that of the scalp in the area where it is implanted, and such that it provides an appreciable surface continuity between an upper face of the case and an upper face of the signal transmission sleeve.

9. The device according to claim 1, wherein the signal transmission sleeve includes an upper face and the case includes an upper face, and wherein the upper face of the signal transmission sleeve is connected to the upper face of the case in continuous fashion, such that it has a roundness closely following a shape of a scalp and/or that of the cranium at an interface between the case and the signal transmission sleeve.

10. The device according to claim 1, wherein a thickness of the signal transmission sleeve is between 1 mm and 3 mm.

11. The device according to claim 1, wherein the signal transmission sleeve has a Shore A hardness less or equal to 50.

12. The device according to claim 1, wherein the case is formed by assembling an upper portion and a lower portion.

13. The device according to claim 12, wherein the upper portion includes a lip extending from an upper face of the case, and defining a lateral surface of the upper portion, where the lip is intended to be inserted in a lower portion of the case, and abuts against a lateral face of the lower portion.

14. The device according to claim 12, wherein the upper portion of the case includes retaining brackets intended to be supported on the cranium of the human or animal.

15. The device according to claim 12, wherein the lower portion has a lower face and a lateral face jointly defining a bowl-shaped recess to hold the electronic circuit.

16. The device according to claim 15, wherein the lateral face of the lower portion is perforated.

17. The device according to claim 1, wherein the case is overmoulded by an overmoulding material.

18. The device according to claim 1, wherein the system of electrodes includes electrodes for recording neural signals and/or stimulation electrodes, and wherein the electronic circuit include means for processing the neural signals measured by the recording electrodes and/or means of production of electrical stimulation signals by the stimulation electrodes.

19. The device according to claim 1, wherein the case is made from a rigid and biocompatible material and wherein the signal transmission sleeve is made from a flexible and biocompatible material.

20. A method for manufacturing a device according to claim 1, wherein a convexity of an upper face of the case of the device is determined from convexity measurements previously made on the cranium of the human or animal.

21. A method of implanting a device according to claim 1 in the cavity formed on the cranium of the human or animal, wherein the device is positioned in the cavity such that an upper face of the case and surface portions of the cranium adjacent to the case form an appreciably continuous surface.

22. An implantable device of a neural interface type for processing signals, including:
    a case intended to be held at least partially in a cavity formed on a cranium of a human or animal,
    an electronic circuit positioned in the case for processing the signals, and
    a system of electrodes coupled electrically to the electronic circuit,
    wherein the system of electrodes is contained in an external perimeter of the case below the electronic circuit.

23. The device according to claim 22, wherein the case includes an upper face, intended to come into contact with skin, a surface of which is appreciably convex.

24. An implantable device of a neural interface type for processing signals, including:
    a case intended to be held at least partially in a cavity formed on a cranium of a human or animal,
    an electronic circuit positioned in the case for processing the signals, and
    a system of electrodes coupled electrically to the electronic circuit,
    wherein the case includes an upper face, intended to come into contact with skin, a surface of which is appreciably convex,
    wherein the case includes a lateral face configured to intersect a curvature of the cranium and/or that of a scalp in an area where it is implanted,
    wherein the lateral face is perforated, and
    wherein the convexity of the upper face of the case is determined from measurements of convexity previously made on the cranium of a human or animal.

* * * * *